United States Patent [19]

Byrd

[11] Patent Number: 5,676,137
[45] Date of Patent: *Oct. 14, 1997

[54] MEDICAL DEVICE SECURING APPARATUS

[76] Inventor: Timothy N. Byrd, 1267 Old Cades Cove Rd., Townsend, Tenn. 37882

[*] Notice: The term of this patent shall not extend beyond the expiration date of Pat. No. 5,501,216.

[21] Appl. No.: 636,976

[22] Filed: Apr. 24, 1996

Related U.S. Application Data

[63] Continuation-in-part of Ser. No. 433,234, May 2, 1995, Pat. No. 5,529,062, which is a continuation-in-part of Ser. No. 344,147, Nov. 23, 1994, Pat. No. 5,501,216.

[51] Int. Cl.$^6$ ................................... A61M 25/02
[52] U.S. Cl. ................... 128/207.17; 128/207.18; 128/207.14; 128/912; 128/DIG. 15; 128/DIG. 26
[58] Field of Search .................. 128/877, DIG. 15, 128/DIG. 26, DIG. 23, 207.17, 207.18, 911, 912, 207.14

[56] References Cited

U.S. PATENT DOCUMENTS

| | | | |
|---|---|---|---|
| D. 310,721 | 9/1990 | Beisang, III | D24/49 |
| 3,046,989 | 7/1962 | Hill | 128/348 |
| 3,297,026 | 1/1967 | Pelt | 128/DIG. 15 |
| 3,826,254 | 7/1974 | Mellor | 128/133 |
| 3,872,860 | 3/1975 | Noblitt | 128/DIG. 15 |
| 3,927,676 | 12/1975 | Schultz | 128/351 |
| 3,977,407 | 8/1976 | Coleman et al. | 128/348 |
| 4,120,304 | 10/1978 | Moor | 128/348 |
| 4,122,857 | 10/1978 | Haerr | 128/348 |
| 4,142,527 | 3/1979 | Garcia | 128/348 |
| 4,249,529 | 2/1981 | Nestor et al. | 128/207.17 |
| 4,331,144 | 5/1982 | Wapner | 128/207.17 |
| 4,333,468 | 6/1982 | Geist | 128/348 |
| 4,351,331 | 9/1982 | Gereg | 128/207.17 |
| 4,414,969 | 11/1983 | Heyman | 128/DIG. 15 |
| 4,489,723 | 12/1984 | Simons et al. | 128/207.16 |
| 4,548,200 | 10/1985 | Wapner | 128/207.17 |
| 4,583,976 | 4/1986 | Ferguson | 604/174 |
| 4,672,722 | 6/1987 | Malamed | 128/DIG. 15 |
| 4,690,675 | 9/1987 | Katz | 604/177 |
| 4,702,736 | 10/1987 | Kalt et al. | 604/180 |
| 4,744,358 | 5/1988 | McGinnis | 128/207.17 |
| 4,774,944 | 10/1988 | Mischinski | 128/207.17 |
| 4,822,342 | 4/1989 | Brawner | 604/180 |
| 4,823,789 | 4/1989 | Beisang, III | 128/207.18 |
| 4,836,200 | 6/1989 | Clark | 128/207.18 |
| 4,932,943 | 6/1990 | Nowak | 604/180 |
| 4,976,700 | 12/1990 | Tollini | 604/180 |
| 5,009,227 | 4/1991 | Nieuwstad | 128/207.17 |
| 5,037,397 | 8/1991 | Kalt et al. | 604/174 |
| 5,215,532 | 6/1993 | Atkinson | 604/180 |
| 5,501,216 | 3/1996 | Byrd | 128/207.17 |

*Primary Examiner*—Vincent Millin
*Assistant Examiner*—V. Srivastava
*Attorney, Agent, or Firm*—Pitts & Brittian, P.C.

[57] ABSTRACT

A medical device securing apparatus for releasably securing at least one medical device to a supporting object. The securing apparatus includes a foundation strap (12) and a securing mechanism for releasably securing the foundation strap to a supporting object (22). An engaging strap (26) extends outwardly from a second end portion (16) of the foundation strap (12) for being received about at least a portion of at least one medical device. Also included is a securing strap (30), secured at its proximal end (31) to the foundation strap (12), for releasably engaging at least a portion of the distal end portion (28) of the engaging strap (26), after the engaging strap has been received about at least a portion of at least one medical device. An adhesive securing mechanism (34, 40) is also provided for releasably securing the distal end portion (28) of the engaging strap (26) between the securing strap (30) and the foundation strap (12), whereby the engaging strap (26) is releasably held in position about at least a portion of at least one medical device.

10 Claims, 4 Drawing Sheets

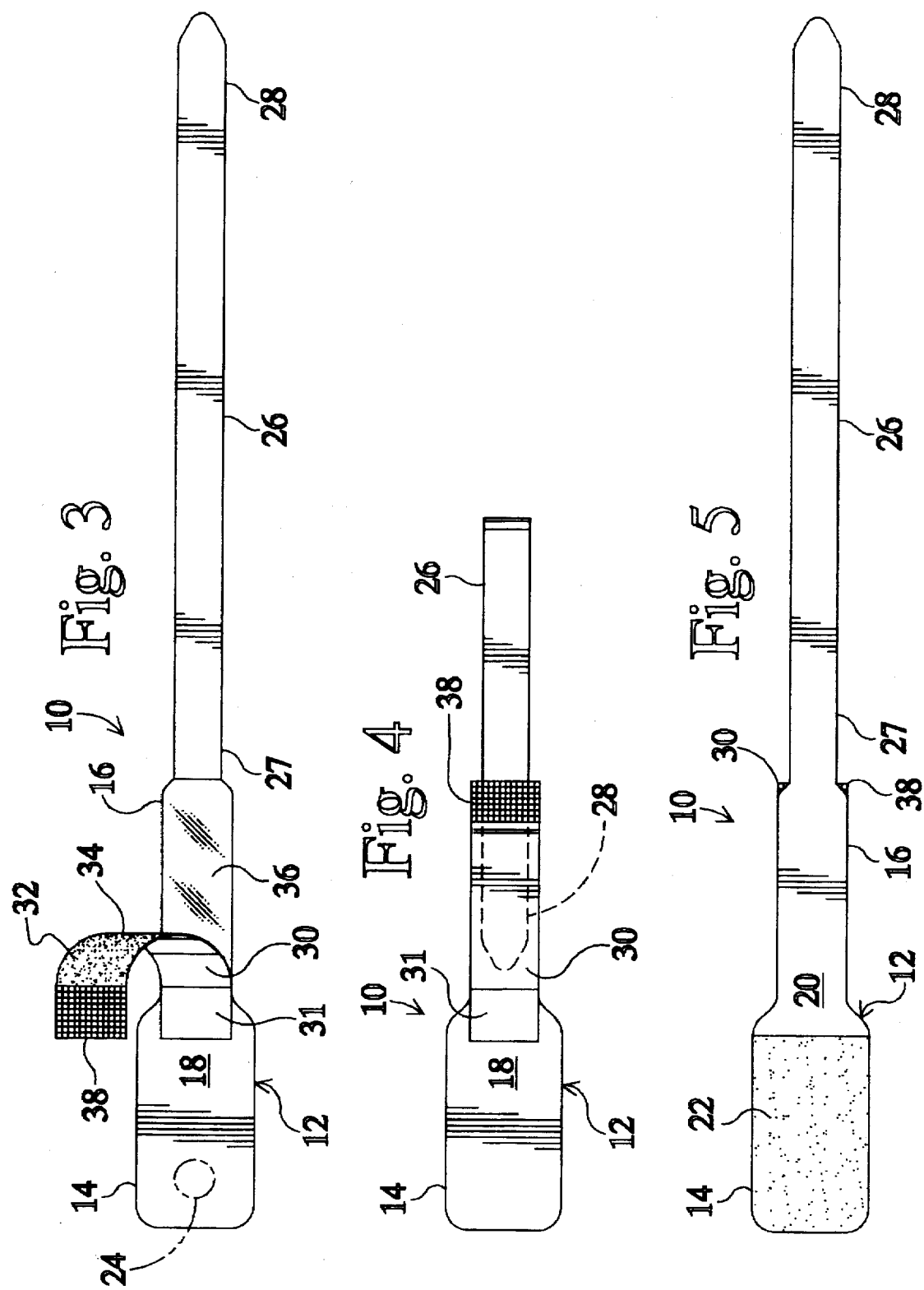

MEDICAL DEVICE SECURING APPARATUS

This application is a continuation-in-part of my U.S. patent application Ser. No. 08/433,234, U.S. Pat. No. 5,529,062 filed May 2, 1995, now under Notice of Allowance, which is a continuation-in-part of my earlier filed application Ser. No. 08/344,147, filed on Nov. 23, 1994, and which issued on Mar. 26, 1996 as U.S. Pat. No. 5,501,216.

TECHNICAL FIELD

This invention relates to an apparatus for releasably securing the position of various medical devices. In this particular invention the securing apparatus includes a flexible foundation strap with an engaging strap extending therefrom. The apparatus also includes a securing strap secured to the foundation strap for releasably securing the distal end of the engaging strap to the foundation strap after the engaging strap has been received around at least a portion of a medical device.

BACKGROUND ART

During the administering of medical care it is common for various medical devices to be secured to supporting structures near a patient, or secured to the patient's skin surfaces. For example, during procedures requiring intubation, it is desirable to secure the position of the tube(s) being used. Accordingly, it is a common practice to secure the tube(s) to the skin of the patient, proximate the point as which the tube(s) enter the body of the patient, with tape or other securing means. Further, it is common for I.V. medication bags to be supported in an elevated position near the patient, and for various monitoring devices to be supported near or on the patient for convenient access. Securing devices have been designed to hold medical devices, but such securing devices tend to be specialized devices which are designed to secure or support a specific medical device, such as a medical tube, and they are not suitable for use in securing a broad range of medical devices. Where the devices are directed toward a broader application they tend to be complex in construction and difficult and/or time consuming to use. In this regard, it is important that health care providers be able to perform medical procedures quickly and efficiently, and securing devices which are difficult and time consuming to use can unnecessarily complicate and/or delay the rendering of medical care. Certain previously known securing devices are disclosed in U.S. Pat. Nos. 5,215,532; 5,037,397; 5,009,227; 4,976,700; 4,932,943; 4,836,200; 4,823,789; 4,822,342; 4,774,944; 4,744,358; 4,702,736; 4,690,675; 4,583,976; 4,548,200; 4,489,723; 4,351,311; 4,333,468; 4,331,144; 4,249,529; 4,142,527; 4,122,857; 4,120,304; 3,977,407; 3,927,676; 3,826,254; 3,046,989; and U.S. Pat. No. Des. 310,721.

Therefore, it is an object of the present invention to provide a medical device securing apparatus for releasably securing a medical device to a supporting object or surface.

It is another object of the present invention to provide a medical device securing apparatus which is easy to use and which allows a medical device to be quickly secured in the apparatus and quickly released from the apparatus.

Yet another object of the present invention is to provide a medical device securing apparatus which can engage, and support a medical device on, various supporting surfaces including the skin of a patient.

Still another object of the present invention is to provide a medical device securing apparatus which is inexpensive to manufacture, yet is suitable for securing a wide range of medical devices.

SUMMARY OF THE INVENTION

The present invention provides a medical device securing apparatus for releasably securing at least one medical device to a supporting object or surface. The securing apparatus includes a foundation strap having first and second end portions and upper and lower surfaces. A securing mechanism for releasably securing said foundation strap to a supporting object is provided. In one embodiment, this securing mechanism is an adhesive surface portion provided on the lower surface of the foundation strap. An engaging strap extends outwardly from the second end portion of the foundation strap for being received about at least a portion of at least one medical device. The securing apparatus also includes a securing strap, secured at its proximal end portion to the foundation strap. The securing strap releasably engages at least a portion of the engaging strap, after the engaging strap has been received about at least a portion of at least one medical device. An adhesive securing mechanism is also provided for releasably securing the distal end portion of the engaging strap between the securing strap and the foundation strap, whereby the engaging strap is releasably held in position about at least a portion of at least one medical device.

BRIEF DESCRIPTION OF THE DRAWINGS

The above mentioned features of the invention will be more clearly understood from the following detailed description of the invention read together with the drawings in which:

FIG. 3 illustrates a top plan view of a medical device securing apparatus of the present invention.

FIG. 4 illustrates a top plan view of a medical device securing apparatus of the present invention.

FIG. 5 illustrates a bottom view of a medical device securing apparatus of the present invention.

BEST MODE FOR CARRYING OUT THE INVENTION

Figure 1:
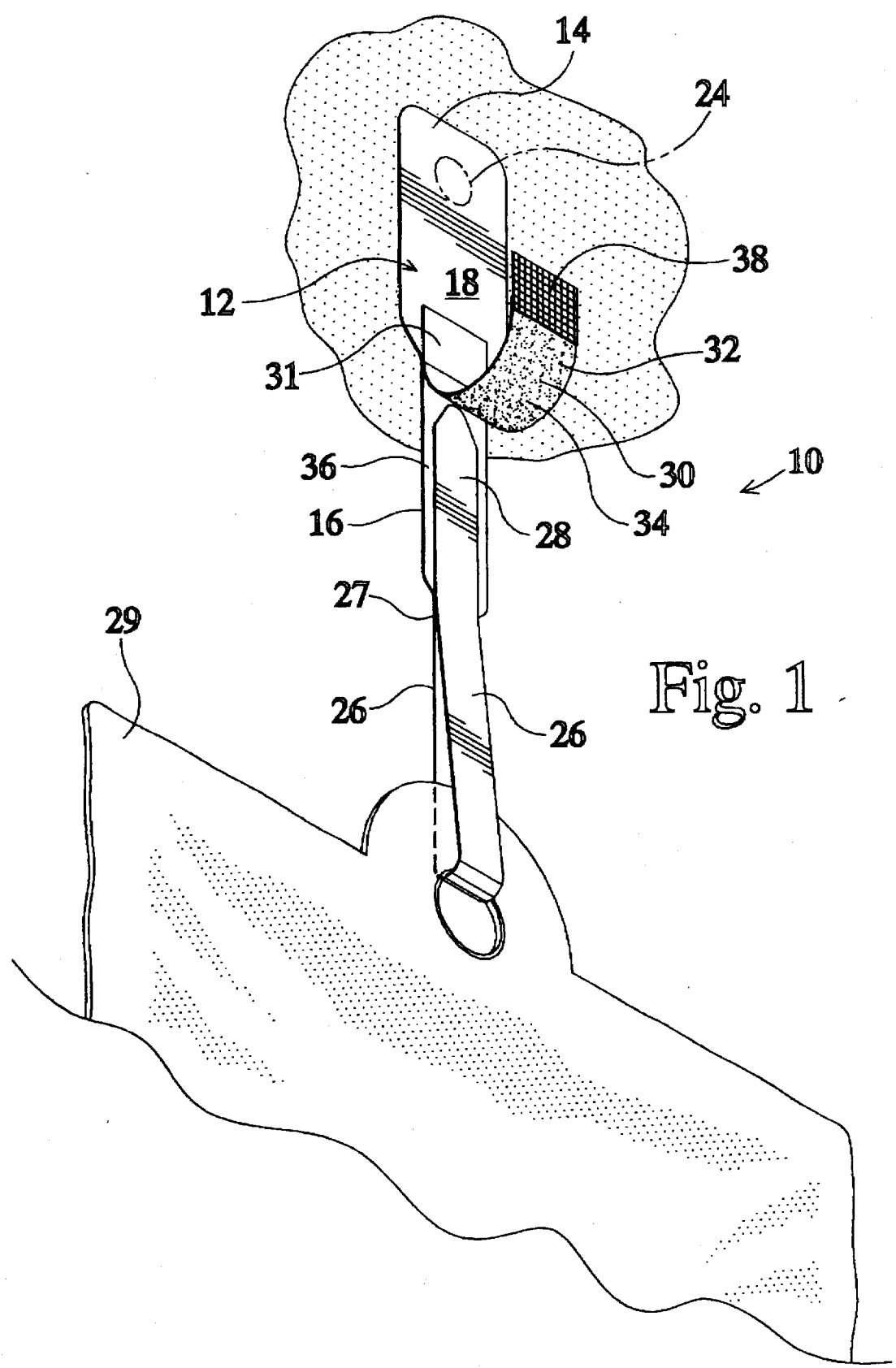
FIG. 1 illustrates a perspective view of a medical device securing apparatus of the present invention.
Figure 2:
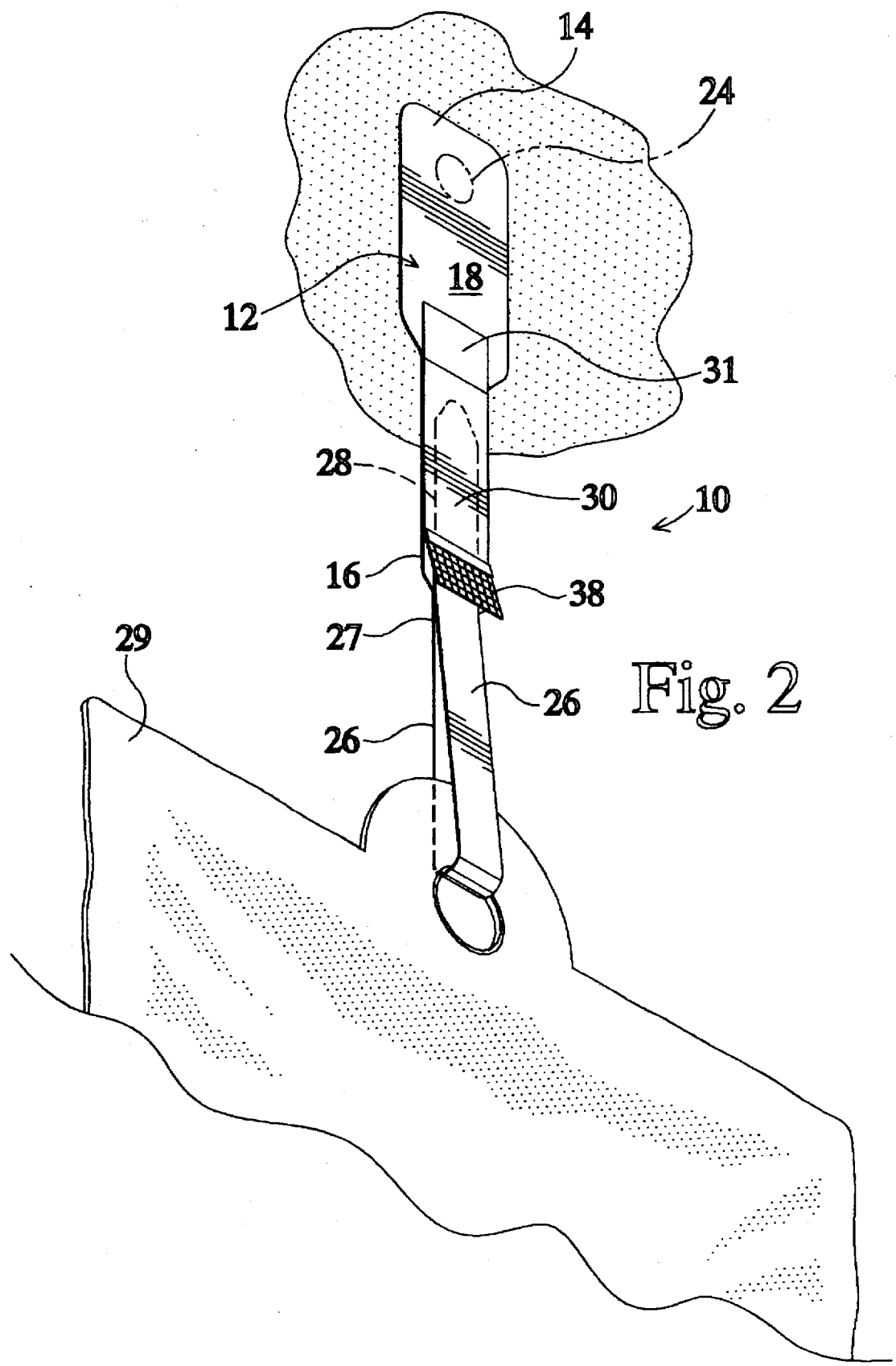
FIG. 2 illustrates a perspective view of a medical device securing apparatus of the present invention.

A medical device securing apparatus incorporating various features of the present invention is illustrated generally at 10 in the Figures. Whereas in FIGS. 1–2 the apparatus 10 is illustrated as being used to secure an I.V. medication bag to a supporting surface, and whereas in FIGS. 6–7, the apparatus 10A is illustrated as securing the position of a plurality of medical tubes, it is contemplated that the apparatus of the present invention can be used to secure various medical devices to other objects or supporting surfaces.

The medical device securing apparatus 10 includes a foundation strap 12. The foundation strap is preferably fabricated of a relatively thin, flexible material, such as, for example, 20 mil. PVC film. It will, however, be understood that other strong, durable fabricating materials can be used if desired. The foundation strap 12 has a first end portion 14 and a second end portion 16, and upper and lower surfaces 18 and 20, respectively. The first end portion 14 of the foundation strap 12 is provided with a securing mechanism for securing the foundation strap 12 to a supporting object. In the preferred illustrated embodiment of FIGS. 1–5 this securing mechanism includes an adhesive covered surface portion 22 disposed on the lower surface 20 of the foundation strap 12 proximate the first end portion 14 of the foundation strap 12. See FIG. 5. Utilizing the adhesive covered surface portion 22, the foundation strap 12 can be releasably bonded to various supporting objects and surfaces, including, without limitation, the skin of a patient, a wall surface, medical equipment, a patient bed, etc.

It is also contemplated that other securing mechanisms can be used, either alone or in combination with the adhesive covered surface portion 21, to secure the foundation strap 12 to a supporting object or surface. For example, the first end portion 14 of the foundation strap 12 can be provided with a hole for receiving a supporting hook or other supporting structure, such as the hole illustrated in phantom lines at 14 in FIGS. 1–3. It is also contemplated that various camps and/or mechanical fasteners can be used as a securing mechanism.

The second end portion 16 of the foundation strap 12 carries a flexible engaging strap 26. The engaging strap 26 defines a proximal end portion 27 secured to the second end portion 16 of the foundation strap 12, and defines a distal end portion 28. Whereas the engaging strap 26 can be a separate component secured at its proximal end portion 17 to the foundation strap 11, it is contemplated that the engaging strap 26 can be integrally formed with the foundation strap 11 to simplify manufacture. The foundation strap 12 is also provided with a securing strap 30 for releasably engaging the engaging strap 26 after the engaging strap 26 has engaged the medical device(s) to be secured. In this regard, the engaging strap 26 is designed to be received through an opening in a medical device, or to be received around a medical device or a portion thereof. For example, in FIGS. 1–2 the engaging strap 26 is received through an opening in an I.V. medication bag 29, and in the alternate embodiment of the invention illustrated in FIGS. 6–7, the engaging strap 26A is received around a plurality of medical tubes 41.

Once the engaging strap 26 has been received about at least one medical device, or a portion thereof, the securing strap 30 is used to releasably secure the distal end portion 28 of the engaging strap 26 to the foundation strap 12 such that the engaging strap 26 is held in position about the medical device(s). More specifically, the securing strap 30 includes a proximal end portion 31 which is secured to the foundation strap 12, and defines an inner surface 32, for engaging the engaging strap 26. An adhesive bonding mechanism is also provided for releasably securing the distal end portion 28 of the tube engaging strap 26 to the securing strap 30. In the preferred illustrated embodiment of FIGS. 1–5, the bonding mechanism includes an adhesive covered surface portion 34 provided on the inner surface 32 of the securing strap 30, and the securing strap 30 is disposed such that it releasably over lays a bonding surface 36 defined by the upper surface 18 of the foundation strap 12. The distal end portion 28 of the tube engaging strap 26 is secured in place by placing the distal end portion 28 on the bonding surface 26, and placing the securing strap 30 over the distal end portion 28 such that the adhesive covered surface portion 34 bonds to the distal end portion 28. In this embodiment the bonding surface 36 is preferably a smooth, non-porous surface which is wider than the distal end portion 28. Also, the securing strap 30 is preferably wider than the distal end portion 28. Accordingly, when the securing strap 30 is secured over the distal end portion 28, portions of the adhesive cover surface portion 34 engage the bonding surface 36 of the foundation strap 12 adjacent to the engaging strap 26, thereby firmly, yet releasably, locking the distal end portion 28 of the engaging strap 26 between the foundation strap 12 and the securing strap 30.

Notwithstanding the firm bonding of the engaging strap 26 between the foundation strap 12 and securing strap 30, the engaging strap 26 can be quickly and easily released by pulling back the securing strap 30 and disengaging it from the engaging strap 26 and the bonding surface 36. In this regard, in the preferred embodiment the securing strap 30 is provided with a pull tab member 38 at its distal end which is free of adhesive and which facilitates the grasping of the securing strap 30 after it has been adhesively bonded to the engaging strap 26 and the bonding surface 36.

Figure 7:
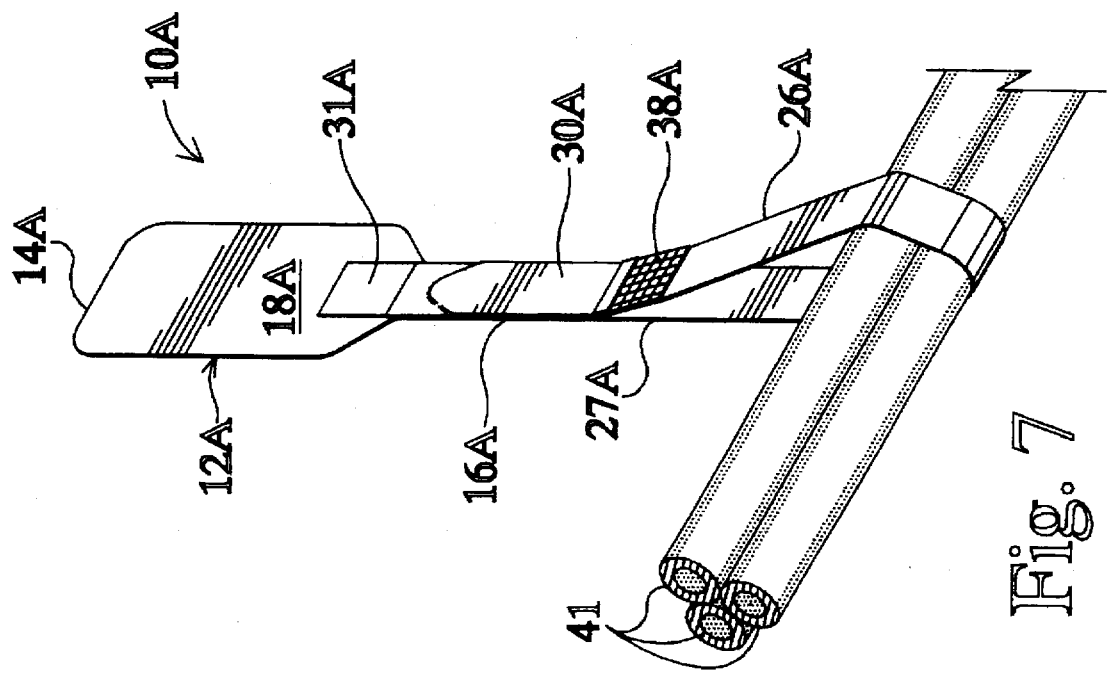
FIG. 7 illustrates a perspective view of an alternate embodiment of the medical device securing apparatus of the present invention.
Figure 6:
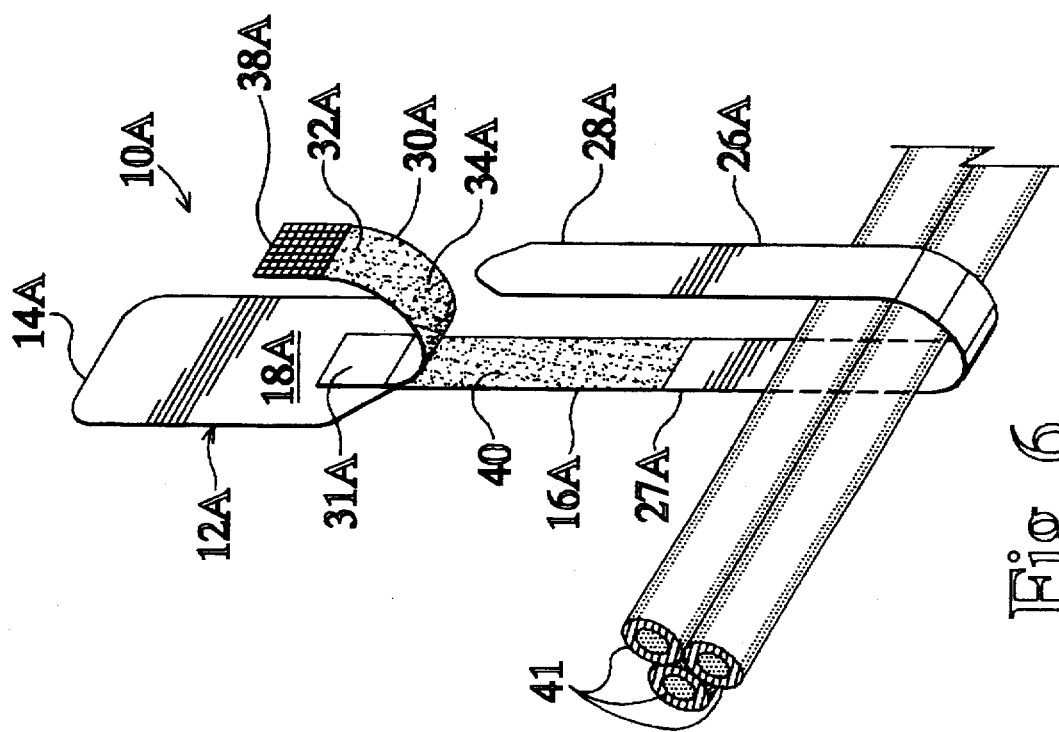
FIG. 6 illustrates a perspective view of an alternate embodiment of the medical device securing apparatus of the present invention.

An alternate embodiment of the medical device securing apparatus is illustrated at 10A in FIGS. 6–7. For convenience, features of the apparatus 10A which are common to the above-described apparatus 10 are referenced with common numerals followed by the alphabetic character "A".

In the embodiment of the apparatus 10A illustrated in FIGS. 6–7, the adhesive mechanism for securing the distal end 28A of the engaging strap 26A also includes an adhesive covered surface portion 40 defined on the upper surface 18A of the foundation strap 12A. In this embodiment both the surface portion 34A and the surface portion 40 adhesively engage the engaging strap 26A to releasably lock the engaging strap 26A between the foundation strap 12A and the securing strap 30A. It will be noted that where the opposing adhesive covered surface portions 34A and 40 are cooperatively used, the desirability of having the securing strap 30A and the foundation strap 12A proximate the surface portion 40 wider than the engaging strap 26A is obviated. Thus, the securing strap 30A, the engaging strap 26A, and the foundation strap 12A proximate the surface portion 40 can be substantially the same width as illustrated in FIGS. 6–7. It will, however, be recognized that the relative widths of the securing strap 30A, the engaging strap 26A, and the foundation strap 12A proximate the surface portion 40 can vary.

In light of the above it will be recognized that the present invention provides a medical device securing apparatus having great advantages over the prior art. The securing apparatus 10, 10A of the present invention can be quickly and easily secured to various supporting object or surfaces, and quickly and easily secured to various medical devices. The medical device which is secured can also be quickly and easily released by simply disengaging the securing strap 30, 30A. However, while a preferred embodiment has been shown and described, it will be understood that there is no intent to limit the invention to such disclosure, but rather it is intended to cover all modifications and alternate constructions failing within the spirit and scope of the invention as defined in the appended claims.

I claim:

1. A medical device securing apparatus for releasably securing a medical device to a supporting object, said securing apparatus comprising:

a foundation strap having first and second end portions and upper and lower surfaces;

a securing mechanism for releasably securing said foundation strap to a supporting object;

an engaging strap extending outwardly from said second end portion of said foundation strap for being received about at least a portion of at least one medical device, said engaging strap defining a distal end portion;

a securing strap for releasably engaging at least a portion of said engaging strap after said engaging strap has been received about at least a portion of at least one medical device; and an adhesive securing mechanism for releasably securing said engaging strap in engagement with said securing strap, whereby said engaging strap is releasably held in position about at least a portion of at least one medical device.

2. The medical device securing apparatus of claim 1 wherein said adhesive securing mechanism includes an adhesive covered surface portion provided on said securing strap.

3. The medical device securing apparatus of claim 2 wherein said foundation strap defines a bonding surface adapted for engaging at least a portion of said distal end portion of said engaging strap and at least a portion of said adhesive covered surface portion provided on said securing strap, and wherein said bonding surface and said adhesive covered surface portion provided on said securing strap are wider than said engaging strap such that said adhesive covered surface portion provided on said securing strap contemporaneously engages at least a portion of said distal end portion of said engaging strap and at least a portion of said bonding surface of said foundation strap.

4. The medical device securing apparatus of claim 1 wherein said adhesive securing mechanism includes a further adhesive covered surface portion provided on said upper surface of said foundation strap, said further adhesive covered surface portion being adapted for releasably engaging at least a portion of said distal end portion of said engaging strap.

5. The medical device securing apparatus of claim 2 wherein said adhesive securing mechanism includes an adhesive covered surface portion provided on said upper surface of said foundation strap, said adhesive covered surface portion of said foundation strap being adapted for releasably engaging at least a portion of said distal end portion of said engaging strap.

6. The medical device securing apparatus of claim 1 wherein said securing mechanism for releasably securing said foundation strap to a supporting object includes an adhesive covered surface portion provided on said lower surface of said foundation strap.

7. A medical device securing apparatus for releasably securing a medical device to a supporting object, said securing apparatus comprising:

a foundation strap having first and second end portions and upper and lower surfaces, said upper surface of said foundation strap being provided with a bonding surface;

a securing mechanism for releasably securing said foundation strap to a supporting object;

an engaging strap extending outwardly from said second end portion of said foundation strap for being received about at least a portion of at least one medical device, said engaging strap defining a distal end portion; and a securing strap for releasably engaging at least a portion of said distal end portion of said engaging strap after said engaging strap has been received about at least a portion of at least one medical device, said securing strap defining a proximal end portion secured to said foundation strap, and having a lower surface provided with an adhesive covered surface portion adapted for contemporaneously engages at least a portion of said distal end portion of said engaging strap and at least a portion of said bonding surface of said foundation strap, whereby said engaging strap is releasably held in position about at least a portion of at least one medical device.

8. The medical device securing apparatus of claim 7 wherein said securing mechanism for releasably securing said foundation strap to a supporting object includes an adhesive covered surface portion provided on said lower surface of said foundation strap.

9. A medical device securing apparatus for releasably securing a medical device to a supporting object, said securing apparatus comprising:

a foundation strap having first and second end portions and upper and lower surfaces, said upper surface of said foundation strap being provided with a first adhesive covered surface portion;

a securing mechanism for releasably securing said foundation strap to a supporting object;

an engaging strap extending outwardly from said second end portion of said foundation strap for being received about at least a portion of at least one medical device, said engaging strap defining a distal end portion, at least a portion of which is releasably bonded to said first adhesive covered surface portion after said engaging strap has been received about at least a portion of at least one medical device; and a securing strap for releasably engaging at least a portion of said distal end portion of said engaging strap after said engaging strap has been received about at least a portion of at least one medical device, said securing strap defining a proximal end portion secured to said foundation strap, and having a lower surface provided with a second adhesive covered surface portion adapted for engaging at least a portion of said distal end portion of said engaging strap, whereby said engaging strap is releasably held in position about at least a portion of at least one medical device.

10. The medical device securing apparatus of claim 9 wherein said securing mechanism for releasably securing said foundation strap to a supporting object includes an adhesive covered surface portion provided on said lower surface of said foundation strap.

* * * * *